United States Patent [19]

Klein et al.

[11] Patent Number: 4,731,534
[45] Date of Patent: Mar. 15, 1988

[54] X-RAY DETECTOR SYSTEM

[75] Inventors: Sigismund Klein, Nuremberg; Wolfgang Ruehle, Erlangen, both of Fed. Rep. of Germany

[73] Assignee: Siemens Aktiengesellschaft, Berlin and Munich, Fed. Rep. of Germany

[21] Appl. No.: 881,608

[22] Filed: Jul. 3, 1986

[30] Foreign Application Priority Data

Jul. 12, 1985 [DE] Fed. Rep. of Germany ....... 3524975

[51] Int. Cl.$^4$ .............................................. G01T 1/20
[52] U.S. Cl. ..................................... 250/366; 250/367
[58] Field of Search ................. 250/363 SH, 363 SA, 250/367, 366, 370 G, 370 J; 378/19

[56] References Cited

U.S. PATENT DOCUMENTS

| 3,509,339 | 4/1970 | Doehner | 250/366 |
|---|---|---|---|
| 4,176,280 | 11/1979 | Greschat et al. | 378/19 |
| 4,292,525 | 9/1981 | Tschunt | 250/367 |
| 4,429,227 | 12/1981 | DiBianca et al. | 250/367 |
| 4,560,877 | 12/1985 | Hoffman | 250/367 |

FOREIGN PATENT DOCUMENTS

| 2814242 | 10/1979 | Fed. Rep. of Germany . |
| 3247204 | 7/1983 | Fed. Rep. of Germany . |
| 2013877 | 8/1979 | United Kingdom . |

Primary Examiner—Carolyn E. Fields
Attorney, Agent, or Firm—Hill, Van Santen, Steadman & Simpson

[57] ABSTRACT

An x-ray detector system has a collimator with a number of spaced walls respectively defining collimator channels therebetween. A detector element is disposed at the end of each collimator channel in the direction of radiation propagation. Each detector element has a radiation transducer contained in a housing. Each transducer has a width which is substantially the same at the width of the collimator channel with which it is associated, and the lateral walls of the detector element housing are substantially in registry with the collimator walls in the direction of radiation propagation, so as to lie within the shadow of the collimator walls. This x-ray detector system thereby achieves a high filling factor.

9 Claims, 2 Drawing Figures

X-RAY DETECTOR SYSTEM

BACKGROUND OF THE INVENTION

1. Field of the Invention

The present invention relates to x-ray detector systems, and in particular to x-ray detector systems having an array of detector elements with a collimator disposed in front of the detector elements in the direction of radiation propagation, with one detector element being associated with each channel in the collimator.

2. Description of the Prior Art

Radiation detector systems are required in most types of x-ray examination devices, particularly devices used in radiographic medical diagnosis wherein an x-ray penetrates a subject under examination and the intensity distribution of the radiation is analyzed. X-ray detector systems used, for example, in computer tomography and computer radiography may have between several hundred and several thousand individual detector elements which are linearly or circularly arranged and directed toward the source of x-rays, such as an x-ray tube. In many installation, a collimator is disposed in the direction of radiation propagation in front of the detector array. The collimator has a plurality of spaced plates consisting of highly radiation absorbent material directed toward the x-ray source for suppressing scattered radiation generated in the measuring field. All x-ray quanta which arrive through the measuring field along a straightline path from the x-ray source should be documented or recorded to as great as extent as possible by the detector system. In order to achieve the best results, as few as possible of the quanta should be lost due to the geometrical structure of the array of detector elements and the collimator. Recording of as many x-ray quanta as is possible is of significant advantage because, given a fixed x-ray power, the number of documented x-ray quanta defines the image quality, among other factors. Although it would be possible, for example, to increase the number of recorded quanta by increasing the radiation dose to the patient, this is undesirable because of possible danger to the patient as well as because of increasing the x-ray tube load. Increasing the x-ray tube load increases the number of movable image artifacts as does lengthening of the exposure times.

A detector system is described in German OS No. 28 40 965 corresponding to U.S. Pat. No. 4,292,525. In this system, the detector array is arranged in an arc around the tube focus, and the detector elements are partially disposed within the collimator channels associated therewith. The wall of the collimator channels shield the detector elements against lateral scattered radiation which may potentially occur.

As particularly seen in FIG. 4 of the U.S. Pat. No. 4,292,525, the radiation permeating a collimator channel is only partially incident on the effective detector surface, i.e., the surface of the scintillation crystal. A not inconsiderable portion of the x-radiation proceeds past the scintillation crystal and is thus no longer available for documentation. The encapsulation of the scintillation crystal forms dead zones in which x-radiation can no longer be detected. A value known as the filling factor is a measure for the x-ray quanta actually incident on the radiation detector surface relative to the total number of x-ray quanta arriving at the detector element. In order to achieve a higher filling factor, it is therefore preferable to avoid the lateral dead zones, i.e., lateral detector regions which no longer register incident radiation, and to increase the effective detector area by enlarging the radiation transducer on which the radiation is incident. A maximum percentage of the x-ray quanta passing through the collimator channels in parallel should thereby be documented.

SUMMARY OF THE INVENTION

It is an object of the present invention to provide an x-ray detector system having a filling factor which is improved over conventional detector systems.

This object is achieved in accordance with the principles of the present invention by arranging the detector elements behind the collimator channels in the direction of radiation propagation such that every transducer is roughly as wide as the collimator channel with which it is associated, and the lateral housing walls for the transducers are disposed in registry with the collimator plates or walls so as to lie in the radiation shadow of the collimator plates.

An increase in the effective detector area is achieved by employing detector elements which, in contrast to prior art elements described above, have a radiation transducer which captures the full amount of radiation permeating a collimator channel. For this purpose, the elements are not disposed in the collimator channels, but are instead disposed at the radiation exit ends of the respective channels. The detector element can be disposed at that location with the transducer occupying at least the width of a collimator channel so that all of the radiation passing through the channel is incident on the transducer. The lateral walls for each detector element are then disposed within the radiation shadow of the collimator plates and thus no longer constitute dead zones.

DESCRIPTION OF THE PREFERRED EMBODIMENTS

Figure 1:
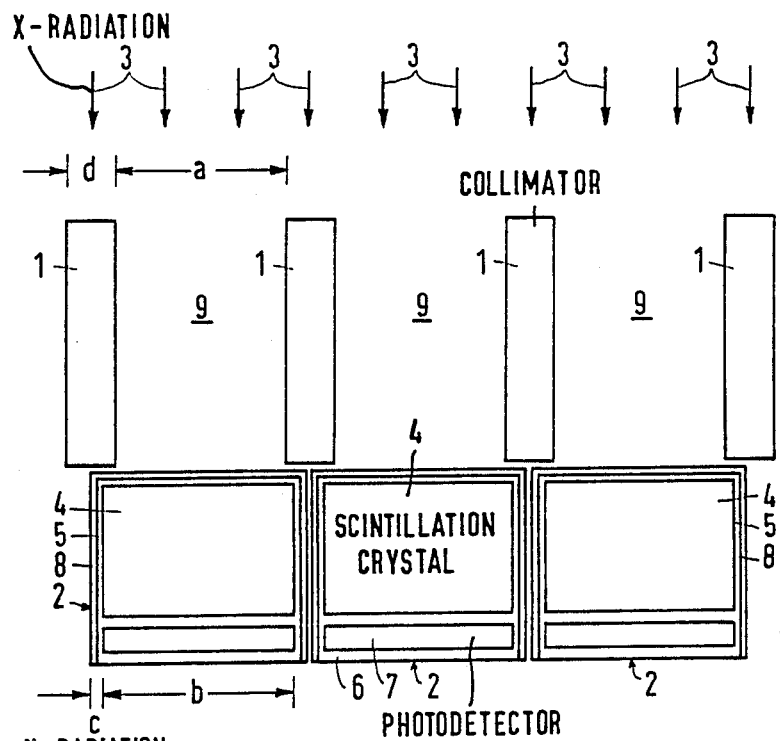
FIG. 1 is a side schematic view of an x-ray detector system constructed in accordance with the principles of the present invention.

An x-ray detector system is shown in FIG. 1 having a collimator with a plurality of spaced collimator plates 1 each having a thickness d defining a plurality of parallel collimator channels 9, each having a width a. A corresponding plurality of detector elements 2 are respectively disposed at each exit end of the collimator channels 9. In the exemplary embodiment shown in FIG. 1, each detector element consists of a radiation detector in the form of a scintillation crystal 4 having a width b which is slightly larger than the distance a between neighboring collimator plates 1. The scintillation crystal 4 is surrounded by a reflector layer 5 at its lateral walls and at the radiation-incident surface thereof. The side of the scintillation crystal 4 facing away from the collimator plates 1 is covered by a silicon photo diode 7 mounted in epoxy resin 6. The entire arrangement is covered by a metallic cladding 8 consisting of, for example, aluminum. The x-ray quanta absorbed by the scintillation crystal 4 which may consist, for example, of sodium iodide, effect an emission of light quanta. The epoxy resin layer 6 is light-transmissive so that the light quanta are incident on the photo diode 7, either directly or after reflection by the reflector 5, and a corresponding electrical signal is generated.

Figure 2:
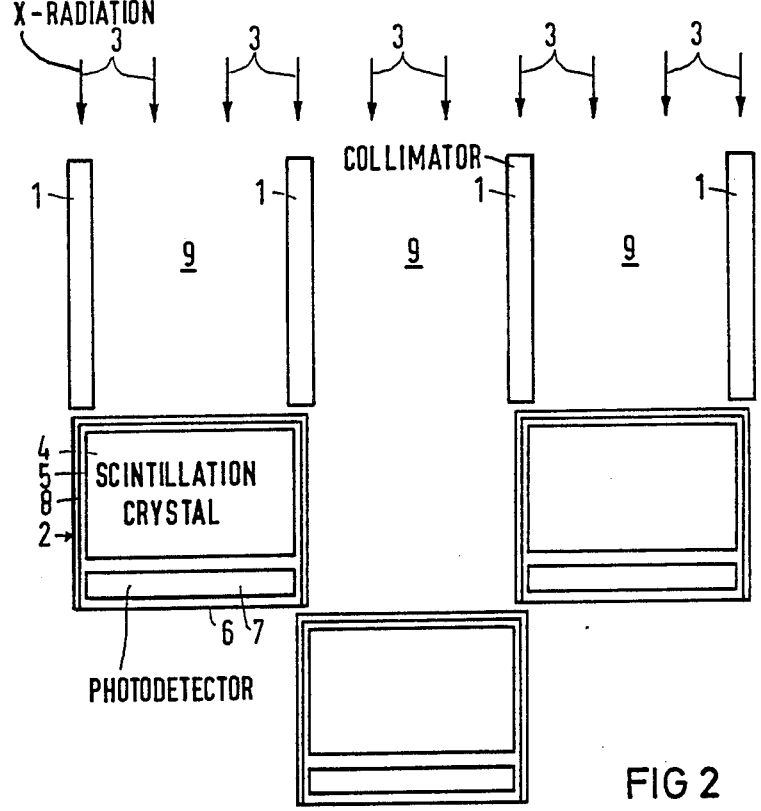
FIG. 2 is a side schematic view of a further embodiment of an x-ray detector system constructed in accordance with the principles of the present invention.

Incident x-radiation 3 permeates the collimator channels 9 parallel to the direction of the collimator plates 1. Scattered radiation which does not proceed parallel thereto is largely suppressed by the highly absorbent collimator plates 1. The dimension c defines the thickness of the encapsulation consisting of the cladding 8 and the reflector layer 5. If the spacing c is selected less than or equal to one-half of the dimension d ($2c \leq d$), the lateral regions of the cladding 8 and the reflector layer 5, which are not effective for detection of x-radiation, are within the radiation shadow of the collimator plates 1. By selecting the active detector width b greater than the spacing a between neighboring collimator plates 1, an additional advantage is achieved in that the lateral edges of the scintillation crystal 4, which are usually less sensitive in this type of detector, also fall within the radiation shadows of the collimator plates 1. If, because of an unusually low thickness of the collimator plates 1, the individual detector elements 2 cannot be arranged linearly next to each other without having the encapsulations emerge from the radiation shadows (i.e., $2c \geq d$), the radiation detectors 2 can be positioned in alternating fashion in two planes as shown in the embodiment of FIG. 2. A further advantage of this embodiment is that by positioning the lateral detector encapsulation walls in registry behind each other, the thickness of the collimator plates can be further reduced, and the width b of the scintillation crystals 4 and of the silicon photo diodes 7 can be made larger. The mechanical stability of these components is thus better than that of the arrangement of FIG. 1. The alternating arrangement is also advantageous when no collimator is used, because the left and right side dead spaces do not add to the overall dead space, but instead overlap.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray detector system comprising:
   a collimator having a plurality of spaced plates defining a plurality of channels through which x-radiation travels, each channel terminating in a radiation exit end; and
   a plurality of detector elements respectively disposed adjacent to the radiation exit ends of said collimator channels, each detector element including a transducer having a surface facing said exit ends effective for detecting x-radiation and further including a housing for said transducer, said housing having lateral walls on opposite sides of said transducer facing said collimator plates and forming a portion of said detector element substantially ineffective for detecting x-radiation at least partially surrounding said transducer surface, said transducer surface having a width substantially equal to the width of the collimator channel and said detector elements being disposed with the respective portions thereof ineffective for detecting radiation in the radiation shadow of said collimator plates.

2. An x-ray detector system as claimed in claim 1 wherein said detector elements are disposed in a common surface side-by-side.

3. An x-ray detector system as claimed in claim 2, wherein said portion ineffective for detecting radiation has a width less than or equal to one-half the width of a collimator plate.

4. An x-ray detector system as claimed in claim 2, wherein said surface is planar.

5. An x-ray detector system as claimed in claim 1, wherein said detector elements are disposed alternatingly in two parallel surfaces offset in the direction of travel of x-radiation through said channels.

6. An x-ray detector system as claimed in claim 5, wherein the respective portions ineffective for detecting radiation of the detector elements in one of said surfaces are in registry with the respective portions ineffective for detecting radiation of the detector elements in the other of said surfaces.

7. An x-ray detector system as claimed in claim 5, wherein said surfaces are planar.

8. An x-ray detector system as claimed in claim 1, wherein each detector element has a cladding surrounding said housing having sides respectively adjacent said lateral walls, and wherein said portion ineffective for detecting radiation is at least partially formed by respective edges of said sides facing a collimator plate.

9. An x-ray detector system comprising:
   a plurality of detector elements alternatingly disposed in parallel surfaces within a radiation path, each detector element having a transducer with an active zone for detecting radiation and a housing having walls surrounding said transducer forming a dead zone substantially ineffective for detecting radiation at least partially surrounding said active zone the dead zones of detector elements in one of said surfaces being disposed in registry with the dead zones of detector elements in the other of said surfaces.

* * * * *